United States Patent [19]

Maeda et al.

[11] 4,431,738

[45] Feb. 14, 1984

[54] METHOD OF PLANT TISSUE AND CELL CULTURE

[75] Inventors: Tadahiko Maeda, Dazaifumachi; Kuniaki Tanaka, Kurume, both of Japan

[73] Assignee: Chlorella Industry Co., Ltd., Tokyo, Japan

[21] Appl. No.: 304,285

[22] Filed: Sep. 21, 1981

[30] Foreign Application Priority Data

Oct. 6, 1980 [JP]  Japan ................................ 55-138718

[51] Int. Cl.³ ........................... C12N 5/00; C12R 1/90
[52] U.S. Cl. ...................................... 435/240; 435/946; 47/1.4; 47/58
[58] Field of Search ................ 435/240, 241, 168, 946; 47/1.4, 58; 71/16, 23

[56] References Cited

U.S. PATENT DOCUMENTS

| | | | |
|---|---|---|---|
| 3,250,606 | 5/1966 | Murray | 47/1.4 |
| 3,520,081 | 7/1970 | Oswald | 435/257 |
| 3,820,281 | 6/1974 | Bigler et al. | 47/1.4 |
| 4,003,156 | 1/1977 | Sibi et al. | 435/240 |

FOREIGN PATENT DOCUMENTS

| | | | |
|---|---|---|---|
| 53-32189 | 3/1978 | Japan | 435/253 |
| 53-149567 | 12/1978 | Japan | 71/23 |

OTHER PUBLICATIONS

Maramorosch et al., Practical Tissue Culture Applications, Academic Press, (1979), p. 29.

Takada et al., "The Growth-Promoting Effect of Extract from Saline-Cultured Chlorella Cells on Halophilic Microorganisms."

Seaweed Symposium Proc. 7, (1972), pp. 329–335.

*Botany,* (Fourth Edition), Wilson and Loomis, p. 400.

*Cell Culture,* (1979), Edited by Jakoby, pp. 299–300.

*Industrial Gums,* (1973), Edited by Whistler, pp. 30 and 87.

*Primary Examiner*—Thomas G. Wiseman
*Assistant Examiner*—John E. Tarcza
*Attorney, Agent, or Firm*—Flynn, Thiel, Boutell & Tanis

[57] ABSTRACT

In a plant tissue and cell cultivation, a method for facilitating both cell multiplication and differentiation is attained by conducting the cultivation in a culture medium containing an extract of micro algae such as Chlorella, Scenedesmus and Spirulina.

11 Claims, 1 Drawing Figure

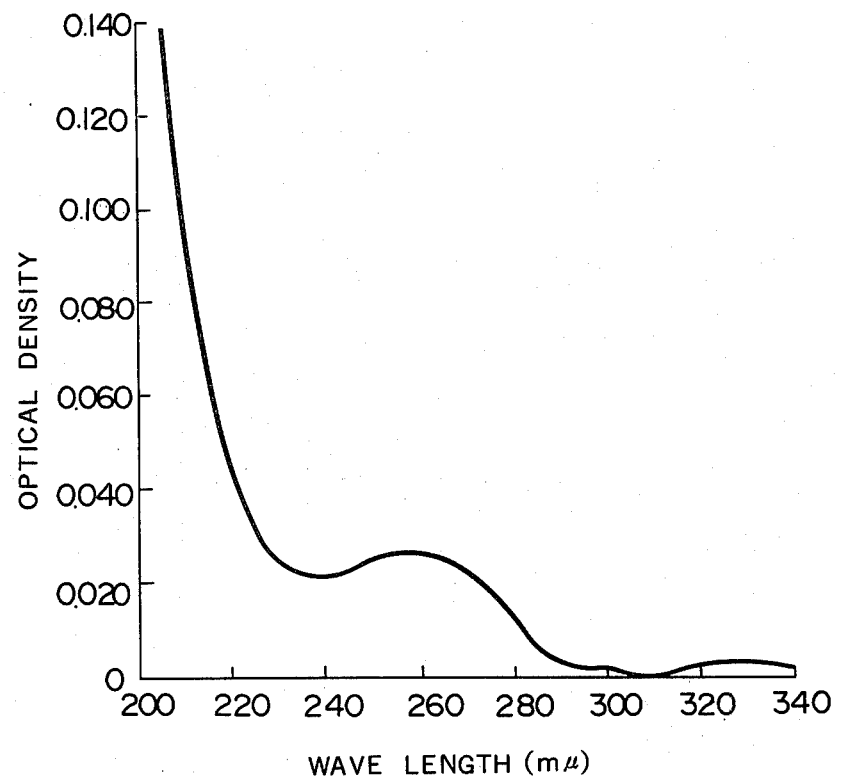

METHOD OF PLANT TISSUE AND CELL CULTURE

BACKGROUND OF THE INVENTION

1. Field of the Invention

The present invention relates to a method of plant tissue and cell culture and more particularly to a method which enables an efficient cultivation of tissue, taken out of an individual plant body or cultivated in a successive cultivation, or plant cells.

2. Description of the Prior Art

When a piece of tissue cut out of a plant body exhibiting relatively rapid growth, such as undifferentiated shoot appex, root cambium and so on, is cultivated in an artificial culture medium, callus formation, which is a phenomenon of undifferentiated cell multiplication, and formation of differentiated foliate parts and roots are observed separately or simultaneously. In such a plant tissue culture, it is often attempted to facilitate culture growth by addition of, coconut milk, yeast extract and the like. Such growth facilitation is limited to causing proliferation of the callus. Therefore, it has not been possible to produce a differentiated plant body without employing any additional measure. Accordingly, it has heretofore been a common practice to incorporate additional measures for facilitating the differentiation, such as for example, irradiation of ultraviolet rays and addition of phytohormones such as indoleacetic acid, benzyladenine and the like in adequate proportion with each other. However, by these prior art methods for accelerating differentiation, the problems have arisen that these methods are difficult to control and, in particular, that synthetic phytohormones may either promote or retard the differentiation depending upon the amount added.

SUMMARY OF THE INVENTION

An object of the present invention is to provide a method for cultivating plant tissue and plant cells which resolves the difficulties of the prior techniques described above.

Another object of the present invention is to provide a method for cultivating plant tissue and plant cells which permits not only the multiplication of plant tissue or cells, but also the differentiation thereof.

A further object of the present invention is to provide a method for cultivating a plant tissue taken out of a normal plant body or a tissue or cells obtained by a successive cultivation of said first generation tissue, which method should permit such cultivation in an efficient manner.

A still further object of the present invention is to provide a method of culture which enables production of plant tissues or cells proliferated by the cultivation or to harvest plant bodies differentiated during the cultivation.

These and other objects of the invention will appear more clearly from the following specification with the accompanying drawing.

The present invention may be summarized as a method of culture of plant tissue and cells which is characterized by cultivating the tissue or cells in a culture medium containing an extract of micro algae.

BRIEF DESCRIPTION OF THE DRAWING

The drawing illustrates an ultraviolet absorption spectrum of the hot water extract of Chlorella to be employed in accordance with the method of the present invention.

DETAILED DESCRIPTION

In this specification, it is meant by the term "micro algae" unicellular algae or their near relatives, such as, for example, Chlorella, Scenedesmus, Spirulina and the like inclusive of natural living and cultivated types.

The extract of micro algae as defined in this specification is an extract which results from an extraction of cells of one or more of said micro algae using an adequate solvent. As the solvent, an aqueous one is especially preferred. Among aqueous solvents, ones such as, for example, water itself and aqueous solutions containing acids, bases and organic solvents dissolved therein may be exemplified.

In order to effect the extraction, algae cells are brought into contact with the solvent which is heated or kept at ordinary temperature. It is preferable to employ a hot water extraction, in which the algae cells are suspended in water in an amount of 1–1,000 grams in dry weight of algae per liter of water and are kept at 50°–150° C. for 0.5–120 minutes, preferably at 100° C. for more than 1 minute, and then are removed from the water by, for example, centrifugation, to obtain an extract. The extract may be refined as necessary by means of, for example, gel filtration, dialysis or the like.

The obtained extract of micro algae contains sugars, proteins, polysaccharides, nucleic acids and other components having molecular weights in the range of from 1,000 to 1,000,000 and exhibits an activity for promoting both multiplication and differentiation in a cultivation of a plant tissue or cells.

The extract obtained as above may be used per se, as a fraction obtained by molecular weight fractionation thereof or a form a concentrate or dry powder obtained by freeze-drying, spray-drying etc. Especially, a high molecular weight fraction obtained by molecular weight fractionation containing nucleic acid and analogous substances, glycoproteins and polysaccharides, etc., and a dry powder thereof are preferred.

According to the present invention, plant tissues and cells are cultivated using a culture medium containing an extract of micro algae. The procedures for preparing the culture, basal culture medium and so on may be identical with those used to form conventional plant tissue cultures. Thus, a known synthetic culture medium containing inorganic salts, micro nutrients, vitamins and so on can be used as the basal culture medium, to which an extract mentioned above is added to perform the culture of plant tissue or cells.

The plant tissue to be cultured includes any tissue taken out of an individual plant body, and particularly parts such as shoot apex, cambium, seedling hypocotyl and the like are preferred. It is also possible to cultivate multiplicated but undifferentiated cells developed in plants, such as callus cells etc., and tissues or cells resulting from successive cultivation may be used as well.

The amount of the micro algae extract to be added to the basal culture medium in accordance with the present invention may be in the range from 1 to 500 mg in dry weight of the extracted matter per liter of medium. The culture medium to which the micro algae extract has been added may be used per se for the cultivation. It is permissible, as in a conventional culture, to incorporate further growth promoting agents such as coconut milk, etc., and differentiation facilitating agents such as synthetic phytohormones, etc., into the medium, in accordance with the specific purpose.

When a plant tissue such as shoot apex is cultivated on a culture medium containing the micro algae extract, not only is the proliferation of callus facilitated, but also the promotion of differentiation is realized, so that a plant body, stem, leaf or root can be developed from the callus, or even developed without callus formation. It is possible to harvest the multiplicated mass of cells and the grown body or parts, or to transplant the differentiated plant body as a seedling. It may also be possible to extract useful substances from the callus obtained. It is furthermore possible to utilize the stem or leaf portions which have been differentiated exclusively.

As described above, the method according to the present invention permits an efficient cultivation of a plant tissue or cells by effecting the multiplication and the differentiation by adding a micro algae extract to the culture medium. It is thereby made possible to realize an application wherein a useful plant is cultivated under a certain condition so as to harvest the cultivated body or cells as such or to extract useful substances therefrom. It may also be possible to attain an idealized and homogeneous seedling culture or even aid the conservation of a plant species.

DESCRIPTION OF THE PREFERRED EMBODIMENT

EXAMPLE 1

Carnation shoot apexes (one of the most rapidly growing tissues in the plant body, including a growing point) were excised out and were each placed on the culture medium, indicated below, in test tubes. The cultivation was conducted under the conditions of a 9 hour illumination period (2,000 X) and 15 hour dark period per day at 25° C. As for the culture medium, a basal culture medium of Murashige & Skoog, the composition of which is given in Table 1, was employed with the exclusion of $FeSO_4$, and thereto were added 2.0% of sucrose, 0.8% of agar-agar and various amounts of Chlorella extract.

TABLE 1

| Basal Culture Medium according to Murashige & Skoog | | | | | |
|---|---|---|---|---|---|
| Inorganic Salts (mg/l) | | Inorgainc Salts (mg/l) | | Vitamins etc. (mg/l) | |
| $NH_4NO_3$ | 1650 | $H_3BO_3$ | 6.2 | Nicotinic acid | 0.5 |
| $KNO_3$ | 1900 | $MnSO_4.4H_2O$ | 22.3 | Pyridoxine-HCl | 0.5 |
| $CaCl_2.2H_2O$ | 440 | $ZnSO_4.7H_2O$ | 8.6 | Thiamine.HCl | 0.1 |
| $MgSO_4.7H_2O$ | 370 | KI | 0.83 | Myo-inositol | 100 |
| $KH_2PO_4$ | 170 | $Na_2MoO_4.2H_2O$ | 0.25 | Glycine | 2 |
| $Na_2$—EDTA | 37.3 | $CuSO_4.5H_2O$ | 0.025 | | |
| $FeSO_4.7H_2O$ | 27.8 | $CoCl_2.6H_2O$ | 0.025 | | |

Each culture medium had a pH of 5.5–6.0. The Chlorella extract had been obtained by dispersing 30 g of Chlorella dry powder in 1 l of water and subjecting the resulting suspension to a hot water extraction at 100° C. for 30 minutes, centrifuging the resulting suspension and freeze-drying the supernatant obtained (4.5 g in dry weight). The ultraviolet absorption spectrum diagram of an aqueous solution of this Chlorella extract is given in the appended drawing. The amount of this Chlorella extract added to each culture medium was one of three amounts, namely, 2, 6 or 20 mg/l. The evaluations of the experimental results for these samples were compared with those obtained without addition of the Chlorella extract.

After cultivation over 2 months, it was confirmed that the group with addition of 20 mg/l of Chlorella extract had shown that most pronounced effect for facilitating both the multiplication and the differentiation. The evaluations of the culture samples were able to classify the samples into 5 ranks from (A) to (E), in which (A) corresponds to the condition that the whole tissue formed callus without differentiation, (B) to the condition that stem and leaf were formed with callused stem, (C) to the condition that stem, leaf and root were formed with callused stem, (D) to the condition that stem, leaf and root were formed without callus formation and (E) to the condition that no multiplication or differentiation was observed.

In Table 2, the results for the tests with addition of Chlorella extract in an amount of 20 mg/l and without addition of Chlorella extract each using 100 test tube samples are summarized by the number of samples in each rank.

TABLE 2

| Experimental Results | | | | | |
|---|---|---|---|---|---|
| | Evaluation | | | | |
| Amount of Chlorella Extr. | (A) | (B) | (C) | (D) | (E) |
| 0 | 22 | 22 | 11 | 34 | 11 |
| 20 mg/l | 15 | 31 | 46 | 8 | 0 |

From these results, a multiplication promoting effect by the addition of the Chlorella extract is recognized, since the numbers of samples in ranks (D) and (E) are smaller for the group with addition of Chlorella extract than the group without addition. Also, a differentiation promoting effect is deduced from the smaller number of samples in rank (A) and the greater number of samples in ranks (B) and (C).

EXAMPLE 2

When a naked rice seed is cultivated on an agar-agar culture medium containing 2.0 mg/l of 2,4-D (2,4 dichlorophenoxyacetic acid) which is a synthetic growth hormone, callus formation will be brought about. In this Example, the influence of addition of Chlorella extract upon the callus formation mentioned above is examined.

Using a basal culture medium B-5 as identified in Table 3, culture mediums of pH 6.0 were prepared by adding 2.0% by weight of sucrose, 2.0 mg/l of 2,4-D, 0.8% by weight of agar-agar and Chlorella extract in various amounts of from 0.1 to 500 mg/l to the basal medium. The cultivation conditions were the same as in Example 1.

TABLE 3

| Basal Culture Medium B-5 | | | |
|---|---|---|---|
| Component | Content | Component | Content |
| $NaH_2PO_4.2H_2O$ | 171.6 mg/l | $Na_2MoO_4.2H_2O$ | 0.2522 mg/l |
| $KNO_3$ | 2527.8 mg/l | $CoCl_2.6H_2O$ | 0.0242 mg/l |
| $(NH_4)_2SO_4$ | 132.1 mg/l | KI | 0.7457 mg/l |
| $MgSO_4.7H_2O$ | 246.5 mg/l | Nicotinic Acid | 1.0 mg/l |
| $CaCl_2.H_2O$ | 111.0 mg/l | Thiamine.HCl | 10.0 mg/l |
| Fe—EDTA | 28 mg/l | Pyridoxine.HCl | 1.0 mg/l |
| $MnSO_4.H_2O$ | 13.6 mg/l | m-Inositol | 100.0 mg/l |
| $ZnSO_4.7H_2O$ | 1.98 mg/l | Sucrose | 20.0 g/l |
| $H_3BO_3$ | 3.03 mg/l | 2,4-D | 2.0 mg/l |
| $CuSO_4$ | 0.0393 mg/l | | |

30 days after the seeds were placed on the culture mediums, evaluation according to the ranks (A) to (E)

of Example 1 was performed. In Table 4, the results for the tests with addition of Chlorella extract in an amount of 10 mg/l and without addition of Chlorella extract are recited.

TABLE 4

| Amount of Chlorella Extr. | Experimental Result Evaluation | | | | |
|---|---|---|---|---|---|
| | (A) | (B) | (C) | (D) | (E) |
| 0 | 86 | 2 | 3 | 0 | 9 |
| 10 mg/l | 54 | 32 | 14 | 0 | 0 |

From the result above, a differentiation promoting effect is recognized, since the numbers of samples in ranks (B) and (C) are greater for the group with addition of Chlorella extract than the group without addition thereof. It was confirmed that a marked effect had been realized by the addition of Chlorella extract in an amount ranging from 1 to 100 mg/l. It was also noticed that although the total number of samples exhibiting cell multiplication were nearly the same for the two groups, the increase in the weight of the grown body was greater for the group with addition of Chlorella extract than the group without addition, wherefrom a proliferation promoting effect was recognized.

What is claimed is:

1. A method for culturing plant cells or plant tissue comprising culturing a piece of tissue excised from a plant body or cells obtained by cultivation of tissue excised from a plant body in a synthetic basal plant tissue culture medium containing an extract of Chlorella effective to cause cell multiplication and cell differentiation of said plant cells or plant tissue.

2. A method according to claim 1, wherein said extract is produced by extraction of said Chlorella with water at a temperature from 50° to 150° C., for from 0.5 to 120 minutes.

3. A method according to claim 1, wherein said extract is produced by extraction of said Chlorella with an aqueous solvent.

4. A method according to claim 3, wherein said aqueous solvent contains dissolved therein an additive selected from the group consisting of an acid, a base, and an organic solvent.

5. A method according to claim 1, wherein said extract comprises substances having molecular weights in the range of 1,000 to 1,000,000, which substances comprise sugars, proteins, polysaccharides and nucleic acids.

6. A method according to claim 1, in which said culture medium contains from 1 to 500 mg of said extract, calculated on a dry basis, per liter of said culture medium.

7. A method according to claim 6, wherein said extract is produced by extracting said Chlorella with water at a temperature of from 50° to 150° C., for from 0.5 to 120 minutes to obtain a crude Chlorella product, and then effecting molecular weight fractionation of said crude Chlorella product to obtain said extract, said extract consisting essentially of nucleic acids, sugars, proteins, and polysaccharides having molecular weights in the range of 1,000 to 1,000,000.

8. A method as claimed in claim 6, wherein the ultraviolet absorption spectrum of said extract displays an optical density minimum at a wavelength of approximately 239 m$\mu$ and an optical density maximum at a wavelength of approximately 258 m$\mu$.

9. A method of plant cell or plant tissue culture comprising:
   suspending cells of Chlorella in an aqueous solvent in an amount of from 1 to 1000 grams in dry weight of said cells per liter of said aqueous solvent;
   maintaining the mixture of said cells and said solvent at a temperature in the range of 50° C. to 150° C. for 0.5 to 120 minutes;
   separating Chlorella cell bodies from said mixture to form an extract from said mixture, said extract being effective to cause cell multiplication and cell differentiation of plant cells or plant tissue;
   adding said extract to a synthetic basal nutritive culture medium for plant cells and plant tissue in an amount of 1 to 500 mg of said extract in dry weight per liter of said medium; and
   cultivating a piece of tissue excised from a plant body or cells obtained by cultivation of tissue excised from a plant body on said culture medium containing said extract to form a plant cell or plant tissue culture.

10. A method for culturing plant tissue and plant cells, which comprises
   (1) providing a solid synthetic basal nutrient culture medium for plant tissue containing, per liter of said culture medium, an amount of an aqueous extract of Chlorella that contains 1 to 500 mg of solids derived from said Chlorella said extract having been prepared by extracting said Chlorella with water at a temperature of from 50° to 150° C., for from 0.5 to 120 minutes, so that said extract contains sugars, proteins, polysaccharides and nucleic acids having molecular weights in the range of from 1,000 to 1,000,000 and exhibits an activity for promoting multiplication and differentiation of plant tissue and plant cells;
   (2) placing and culturing on said culture medium a piece of tissue excised from a plant body or cells obtained by cultivation of tissue excised from a plant body until a callus is formed, followed by the formation of stems and leaves, or stems, leaves and roots.

11. A method as claimed in claim 10, wherein said algae is extracted with water at a temperature of 100° C. for at least 1 minute.

* * * * *